United States Patent
Chan

(10) Patent No.: US 8,045,173 B2
(45) Date of Patent: Oct. 25, 2011

(54) ADAPTIVE LINEAR FILTER FOR REAL TIME NOISE REDUCTION IN SURFACE PLASMON RESONANCE SYSTEMS

(75) Inventor: David So Keung Chan, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 225 days.

(21) Appl. No.: 12/535,371

(22) Filed: Aug. 4, 2009

(65) Prior Publication Data

US 2011/0032527 A1 Feb. 10, 2011

(51) Int. Cl.
*G01N 21/55* (2006.01)
(52) U.S. Cl. ........................................ 356/445; 356/448
(58) Field of Classification Search .......... 356/445–448, 356/128–137; 436/518, 525; 422/82.05, 422/82.07, 82.08; 435/288.7; 385/12
See application file for complete search history.

(56) References Cited

U.S. PATENT DOCUMENTS

| 7,012,694 B2 | 3/2006 | Ivarsson |
| 7,230,714 B2 | 6/2007 | Barford et al. |
| 7,251,085 B2 | 7/2007 | Bahatt et al. |

FOREIGN PATENT DOCUMENTS
WO 97/15819 A1 5/1997

*Primary Examiner* — Tri T Ton
(74) *Attorney, Agent, or Firm* — Jenifer E. Haeckl

(57) ABSTRACT

A method for linear filtering of noise in a SPR sensorgram generated from a surface plasmon resonance apparatus is provided. The method includes providing a linear filter of variable length to filter an output signal in the sensorgram. The method further includes determining an optimal length of the linear filter based on a slope of the signal in the sensorgram and multiple timing of occurrences of events during measurement of refractive index in the apparatus to reduce noise in the sensorgram.

20 Claims, 7 Drawing Sheets

ADAPTIVE LINEAR FILTER FOR REAL TIME NOISE REDUCTION IN SURFACE PLASMON RESONANCE SYSTEMS

BACKGROUND

The invention relates generally to a filtering scheme for noise reduction in Surface Plasmon Resonance (SPR) sensorgrams and more particularly, to an adaptive linear filtering scheme for noise reduction in SPR sensorgrams.

A surface plasmon resonance (SPR) measurement system typically presents detected changes in the refractive index of a sample in the form of a sensorgram. A sensorgram is a biomolecular interaction plot of the relative refractive index of the sample versus time and may contain one or more phases. Each phase of the plot includes a buffer-only period followed by association and dissociation periods. The association and dissociation periods include adsorption and desorption of biomolecules resulting in a change in refractive index. The adsorption-desorption can be followed in real-time and the amount of adsorbed species can be determined. The SPR sensorgrams may contain different types of noise components that can mask or otherwise distort features of the sensorgrams. The noise components may be attributed to measurement uncertainty in an optical apparatus of the SPR measurement system. The noise components may also be due to mechanical events such as the opening or closing of valves that control the flow of buffer and analytes in the samples. Furthermore, there may be drift in the measurements due to temperature variations or sample non-uniformities.

Various schemes have been investigated for noise reduction in SPR sensorgrams, including linear and nonlinear filtering. Linear filtering can be very effective in reducing random noise components present in a signal. However, convention linear filtering has been noted to have several shortcomings. When conventional linear filtering, such as lowpass filtering, is applied to an SPR sensorgram, high frequency features, such as sharp transitions in the sensorgram, may be smoothed out, or eliminated. Yet these sharp transitions may be indicative of a critical biochemical process or event, such as the onset of a binding event between analytes and ligands within the sample. Smoothing out or eliminating these sharp transitions can make determination of association/dissociation rates and other important indicators of biochemical processes more difficult or less accurate. Conventional linear filtering can also result in ringing when a signal includes discontinuities or other anomalies, making biochemical processes or events depicted in the SPR sensorgram difficult to interpret.

Therefore, it is desirable to have a linear filtering method for reducing noise while preserving important signal characteristics in SPR sensorgrams.

BRIEF DESCRIPTION

In accordance with an embodiment of the invention, a method for linear filtering of noise in a SPR sensorgram generated from a surface plasmon resonance apparatus is provided. The method includes providing a linear filter of variable length to filter an output signal in the sensorgram. The method further includes determining an optimal length of the linear filter based on a slope of the signal in the sensorgram and multiple timing of occurrences of events. Thus, the method includes determining an adaptive filter length in real-time during measurement of refractive index in the apparatus for reducing noise in the sensorgram.

In accordance with another embodiment of the invention, a method for linear filtering of noise in a sensorgram generated from a surface plasmon resonance apparatus is provided. The method includes providing a linear filter of variable length to filter an output signal in the sensorgram. The method further includes determining a first filter length based on multiple timings of occurrences of events during measurement of surface plasmon resonance in the apparatus. The method also includes determining a second filter length based on a slope of the signal between the events. Further, the method includes comparing the first filter length and the second filter length and selecting a shorter length from either the first filter length or the second filter length.

In accordance with yet another embodiment of the invention, a linear filtering system for filtering noise in a surface plasmon resonance sensorgram is provided. The system includes a SPR measurement apparatus for generating a sensorgram. The system also includes a processor for receiving the sensorgram. The processor is configured to provide a linear filter of variable length to filter an output signal in the sensorgram. The processor further determines a first filter length based on multiple timings of occurrences of events during measurement of surface plasmon resonance in the apparatus. The processor also determines a second filter length based on a slope of a signal between the multiple events. Furthermore, the processor compares the first filter length and the second filter length and selects a shorter length between the first filter length and the second filter length.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the invention are directed towards an adaptive linear filtering method for noise reduction in SPR sensorgrams. The method includes providing a linear filter of variable length to filter an output signal in the sensorgram. As used herein, the term 'adaptive' refers to the dynamic variation of the linear filter for ensuring that the output signal in the sensorgram is preserved.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of operating parameters are not exclusive of other parameters of the disclosed embodiments.

Figure 1:
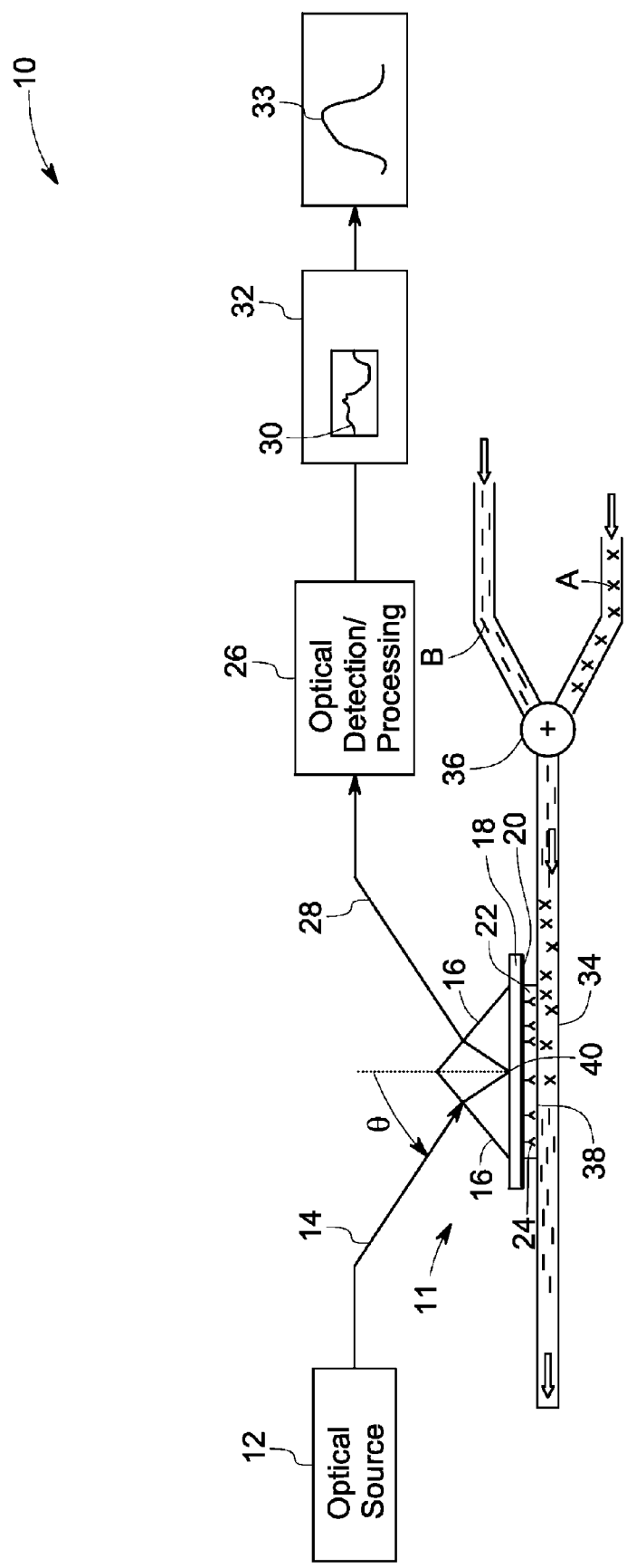
FIG. 1 illustrates a SPR measurement apparatus in accordance with an exemplary embodiment of the invention.

FIG. 1 illustrates an exemplary linear filtering system 10 employed in a SPR measurement apparatus 11. The apparatus 11 is a conventional SPR measurement apparatus for generating a sensorgram. The SPR measurement apparatus 11 includes an optical source 12 that provides optical stimuli 14 to a prism 16 at various angles of incidence ⊖ relative to the prism 16. In the illustrated embodiment, the SPR measurement apparatus 10 uses angle-based SPR. In another embodiment, the SPR measurement apparatus 10 employs wavelength based SPR in which the optical source 12 provides optical stimuli 14 to the prism 16 using multiple optical wavelengths. The prism 16 further includes a glass slide 18 with a thin optically reflective substrate 20 such as a gold film and a binding layer 22 that includes ligands 24. In one embodiment, the binding layer 22 is a dielectric layer. The apparatus 11 also includes an optical detection-processing unit 26 that intercepts reflected optical signals 28 that are reflected from the prism 16. The reflected optical signals 28 are further processed by the detection-processing unit 26 to provide a SPR sensorgram 30 at an output device 32. The SPR sensorgram is linearly filtered to generate an output signal that represents a filtered SPR sensorgram 33.

Furthermore, the SPR measurement apparatus 10 has a flow channel 34 through which analytes A and buffer B are alternately flowed past the binding layer 22. The flow of the analytes A and buffer B are controlled using a valve 36 coupled to the channel 34. The positions of the prism interface 38 wherein the optical stimuli 14 are incident may be referred to as targets 40. When the optical stimuli 14 are incident on multiple targets 40 in the prism interface 38, multiple SPR sensorgrams 30 can be provided by the SPR measurement apparatus 10, wherein each SPR sensorgram 30 corresponds to a designated one of the multiple targets 40. The detection-processing unit 26 may also include a processor for receiving the SPR sensorgram 30. The processor may be configured to implement the adaptive linear filtering scheme for noise reduction in SPR sensorgrams 30 and provide the filtered SPR sensorgram 33 in the output device 32.

It should be noted that embodiments of the invention are not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

Features of the SPR sensorgrams 30 depict phases that represent various physical or biochemical events occurring at the prism interface 38. In operation, the phenomenon of surface plasmon resonance occurs when light is reflected off the reflective substrate 20. A fraction of the light energy (optical stimuli 14) incident at a sharply defined angle may interact with delocalized electrons in the reflective substrate 20 such as metal film, thus reducing the reflected light intensity. The precise angle of incidence at which this occurs is determined by the refractive index close to the backside of the metal film, to which target molecules (analytes A) are immobilized and arrested by the ligands 24 in a mobile phase running along the flow channel 34. If binding occurs to the ligands 24 the local refractive index changes, leading to a change in SPR angle, which is monitored in real-time by detecting changes in the intensity of the reflected optical signals 28, producing the sensorgram 30. The rates of change of the SPR signal are analyzed by the detection-processing unit 26 to yield apparent rate constants for the association and dissociation phases of the interaction at the prism interface 38. The ratio of these values gives an apparent equilibrium constant. The size of the change in SPR signal is directly proportional to the analytes being immobilized and thus, may be interpreted in terms of the stoichiometry of the interaction.

Figure 2:
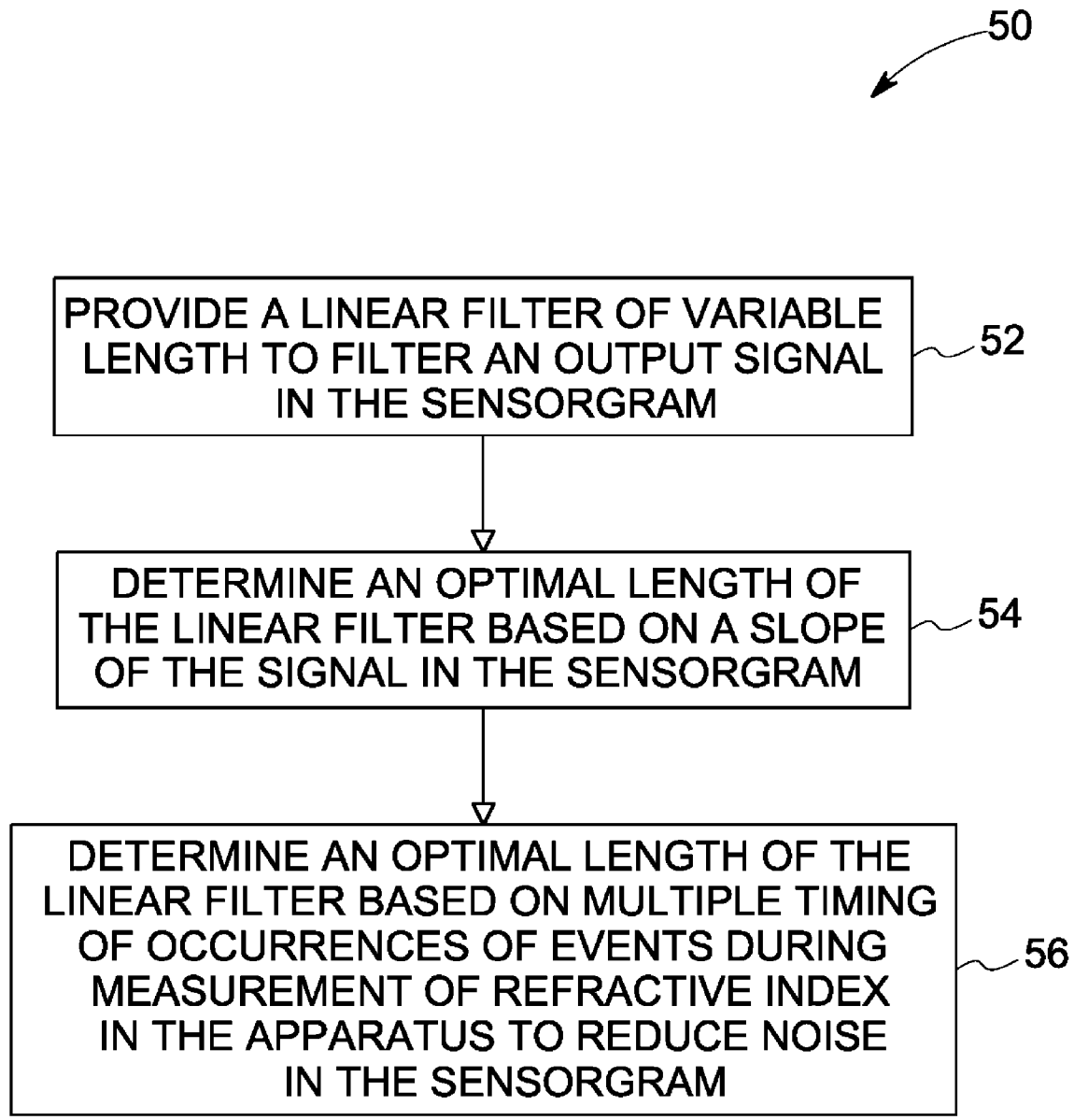
FIG. 2 is a flow chart of a linear filtering method in accordance with an exemplary embodiment of the invention.

FIG. 2 shows a flow chart of a linear filtering method 50 employed in FIG. 1. As discussed, the linear filtering method 50 reduces the noise components in the SPR sensorgram but also retains the effectiveness of the SPR signal. This linear filtering method 50 provides for a linear filter of variable length to filter the output signal in the SPR sensorgram at step 52. In one embodiment, the linear filter includes a symmetric finite impulse response (FIR) filter. The symmetric FIR filter length may vary in response to variation of the output signal. In a non-limiting example, the method 50 provides for a long filter length in response to an output signal with decreasing variation. The method 50 also provides for a short filter length in response to an output signal with increasing variation. The symmetric filter length is, therefore, an adaptive moving average filter length that varies dynamically in length for ensuring the output signal characteristics are preserved. The output signal characteristics are substantially indicative of critical biochemical process and therefore, retaining the characteristics is of utmost significance for accurate analysis of such biochemical processes. At step 54, the linear filtering method 50 provides for determining an optimal length of the linear filter based on a slope of the signal in the SPR sensorgram. Further, at step 56, the linear filtering method 50 includes determining an optimal filter length based on multiple timing of occurrences of events during measurement of refractive index in the SPR apparatus to reduce noise in the SPR sensorgram. The events are substantially indicative of a start of association and dissociation of reactants in the biochemical process. Non-limiting examples of such events may include opening and closing of valves, distances between multiple valves, distances between multiple transducers and flow rates of buffer or analytes in the SPR apparatus 11 of FIG. 1.

Figure 3:
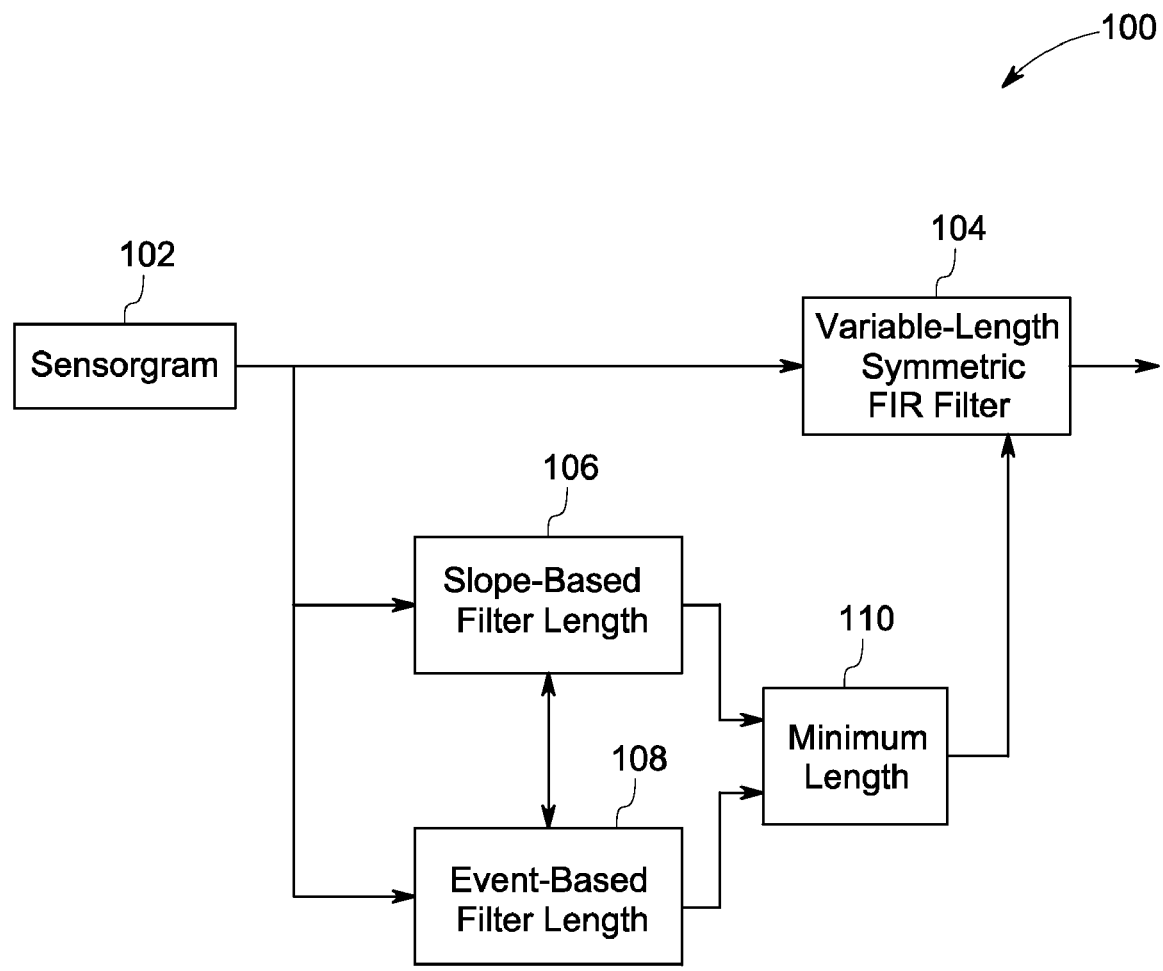
FIG. 3 is a schematic block diagram illustrating a filtering algorithm in accordance with an exemplary embodiment of the invention.

FIG. 3 is a schematic block diagram representation of an overall linear filtering algorithm 100 taking into account slope of the sensorgram 30 (FIG. 1) and occurrence of events in the SPR measurement apparatus. The filtering algorithm 100 includes an input SPR sensorgram 102 and an adaptive filter 104 for filtering random noise components in the SPR sensorgram 102. The adaptive filter 104 is a variable-length FIR filter. The instantaneous length of the adaptive filter 104 is determined in real time by two different methods including a slope-based method 106 and an event-based method 108. The filtering algorithm 100 runs in real-time, wherein the output (instantaneous filter length) is delayed by a specified amount of time from the input. The instantaneous filter length determined is the minimum of the length determined by the two methods as shown in block 110. The two methods depicted by blocks 106 and 108 include auxiliary information of events occurring in the SPR measurement apparatus 10 as shown in FIG. 1.

The slope-based method of block 106 provides for an estimate of the instantaneous slope of the signal. The slope-based method determines the filter length that limits signal distortion in regions between the events while maximizing noise reduction. It may be noted that reducing distortion and reducing noise are conflicting goals, since increasing filter length increases noise reduction and also increases signal distortion for a fixed non-zero rate of slope change. The distortion increases proportionally to the rate of slope change even for a fixed filter length. Thus, the slope-based method 106 includes auxiliary information of the output signal between the events in the SPR sensorgram to reduce filter length as the rate of change in signal slope increases, even though at the expense of reduced noise suppression. This auxiliary information of the nature of signal between the events is a first order equation of the form:

$$s(t)=W(X+Ye^{-\alpha t})+Z \quad (1)$$

During association event, the constants X=1, Y=−1, and $\alpha=k_a C+k_d$, whereas during dissociation event, X=0, Y=1, and $\alpha=k_d$. The constants used in the above equation, namely $k_a$ and $k_d$ are association and dissociation rate constants respectively, whereas C is the concentration of analytes in the sample. For any given rate constant $\alpha$, the rate of change of the slope of s(t) is proportional to the slope itself, such that the rate of slope change is inferred by estimation of the slope. This is achieved by a combination of a short-window slope estimator that responds quickly to signal changes, and a Kalman slope estimator that produces a more accurate estimate of slope in absence of abrupt changes. Both the short-window and the Kalman slope estimator includes efficient recursive filters that estimates the state of a linear dynamic system from a series of noisy measurements.

On the other hand, the event-based method represented by block 108 provides for an estimation of the significance of events, such as the start of association or dissociation in the SPR measurement apparatus. The event-based method represented by block 108 determines timings of multiple key events such as opening and closing of valve 36 (FIG. 1), flow rates in the flow channel 34 and distances between the valve and the binding layer 22 in the SPR apparatus 10. The event-based method represented by block 108 determines a filter length that preserves abrupt signal changes around event times and minimizes the impact on adjacent filtered results. This is achieved by building barriers around event times such that abrupt changes within these barriers are prevented both from being smoothed out and from distorting results outside the barriers. The length of the region between barriers depends on the uncertainty of the event timing, and can be extended to include noise bursts associated with injection events. The injection events may be referred to as opening of valves for flowing buffer B or analytes A through the flow channel 34 (FIG. 1). The filter length is reduced linearly as the barriers are approached from either side, to a minimum length that is dependent on the estimated significance of the event. At the limit of maximum significance, the length is reduced to one, implying the data within the barriers are not filtered at all, and has no influence on results outside the barriers.

Figure 4:
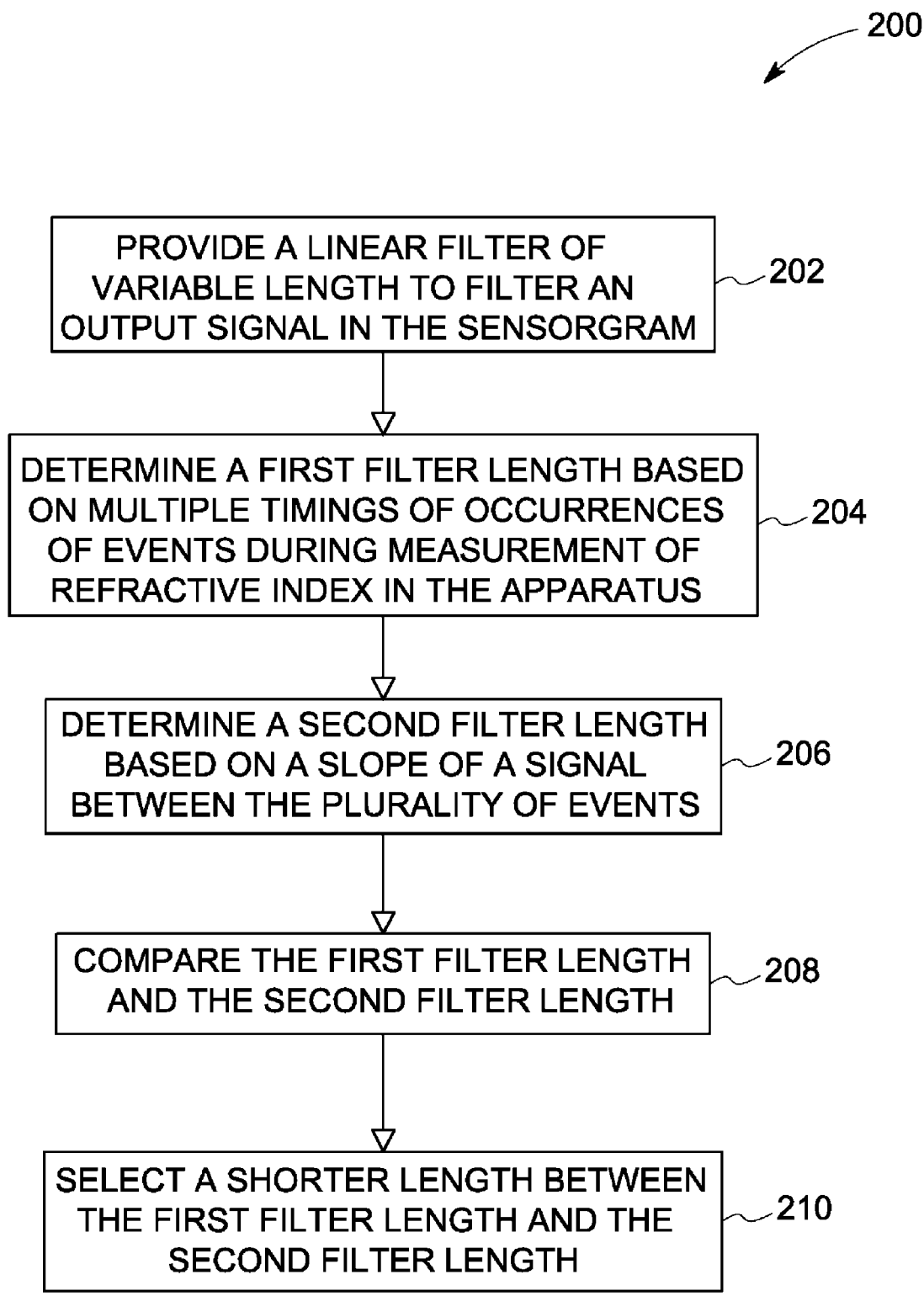
FIG. 4 is a flow chart for determining an optimal filter length in real time for the linear filtering method in accordance with an exemplary embodiment of the invention.

FIG. 4 shows a flow chart for determining an optimal filter length in real time for the linear filtering method 200 in accordance with another embodiment of the invention. At step 202, the linear filtering method 200 includes providing a linear filter of variable length to filter an output signal in the SPR sensorgram. The linear filtering method 200 further includes determining a first filter length based on multiple timings of occurrences of events during measurement of surface plasmon resonance in the SPR apparatus at step 204. Thus, the linear filtering method 200 provides for the first filter length based on determining multiple event times and estimating the significance of the events. Further, at step 206, the linear filtering method 200 includes determining a second filter length based on a slope of the signal between the events. At step 208, the linear filtering method 200 includes comparing the first filter length and the second filter length and finally selecting a shorter length from either the first filter length or the second filter length at step 210. The filtering method 200 includes a filtering algorithm (FIG. 3) that runs in real time but the output is delayed from an input by a specified amount. Filtering performance increases as the allowed time delay increases.

EXAMPLES

The examples that follow are merely illustrative and should not be construed to limit the scope of the claimed invention.

Figure 5:
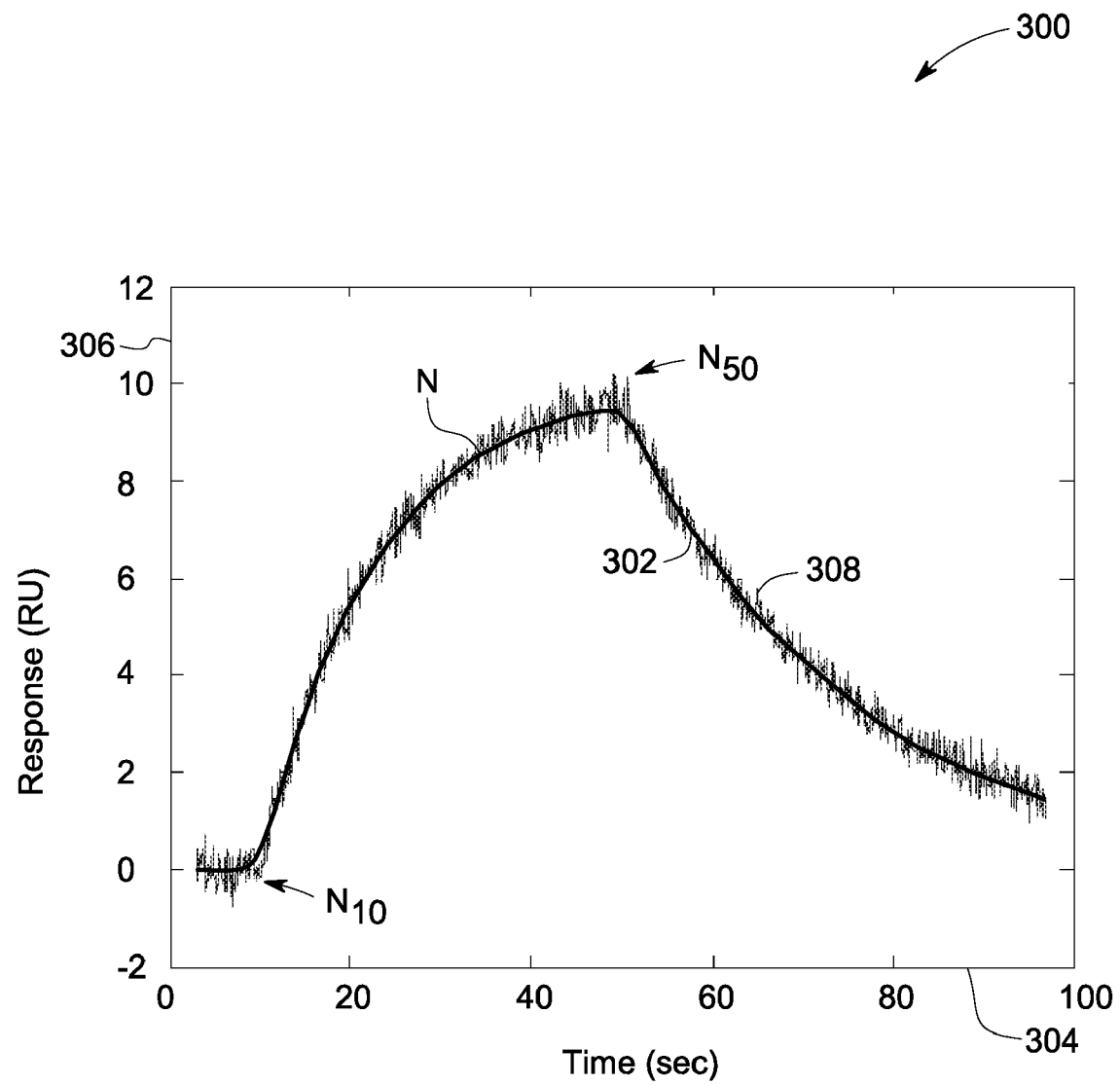
FIG. 5 is an exemplary graphical illustration of a SPR sensorgram with a filtered output associated in accordance with an embodiment of the present invention.

FIG. 5 is a graphical illustration 300 of a SPR sensorgram with a filtered output 302 in accordance with an exemplary embodiment of the present invention. The SPR sensorgram shown is a plot of refractive index versus time. The X-axis 304 represents time in seconds. The Y-axis 306 represents refractive index intensity measured as response units (RU). The refractive index intensity is a measure of the binding capacity of analytes in the binding layer of the SPR measurement apparatus. As illustrated herein, the filtered output 302 is overlaid on unfiltered input signals 308 of the SPR sensorgram. In the present example, an input sample time is 0.1 seconds with an allowed time delay of 3 seconds. The maximum filter length is 61 samples and binding capacity is 20 response units (RU). The present example is chosen for its relatively low value of the maximum binding capacity (i.e. maximum 12 RU in the Y-axis). Since noise N as a percentage of signal decreases as the binding capacity increases, noise filtering is of lesser significance at higher values of the binding capacity. Further, the example includes $k_a C=k_d=0.04$ and bulk response=0. The result in the illustrated example is similar to a result of filtering with a moving average filter with fixed length of 61 samples except in the regions ($N_{10}$ and $N_{50}$) around and immediately after the start of association at 10 seconds and dissociation at 50 seconds. At these event times, the adaptive filter of the present example follows the signal change with improved accuracy.

Figure 6:
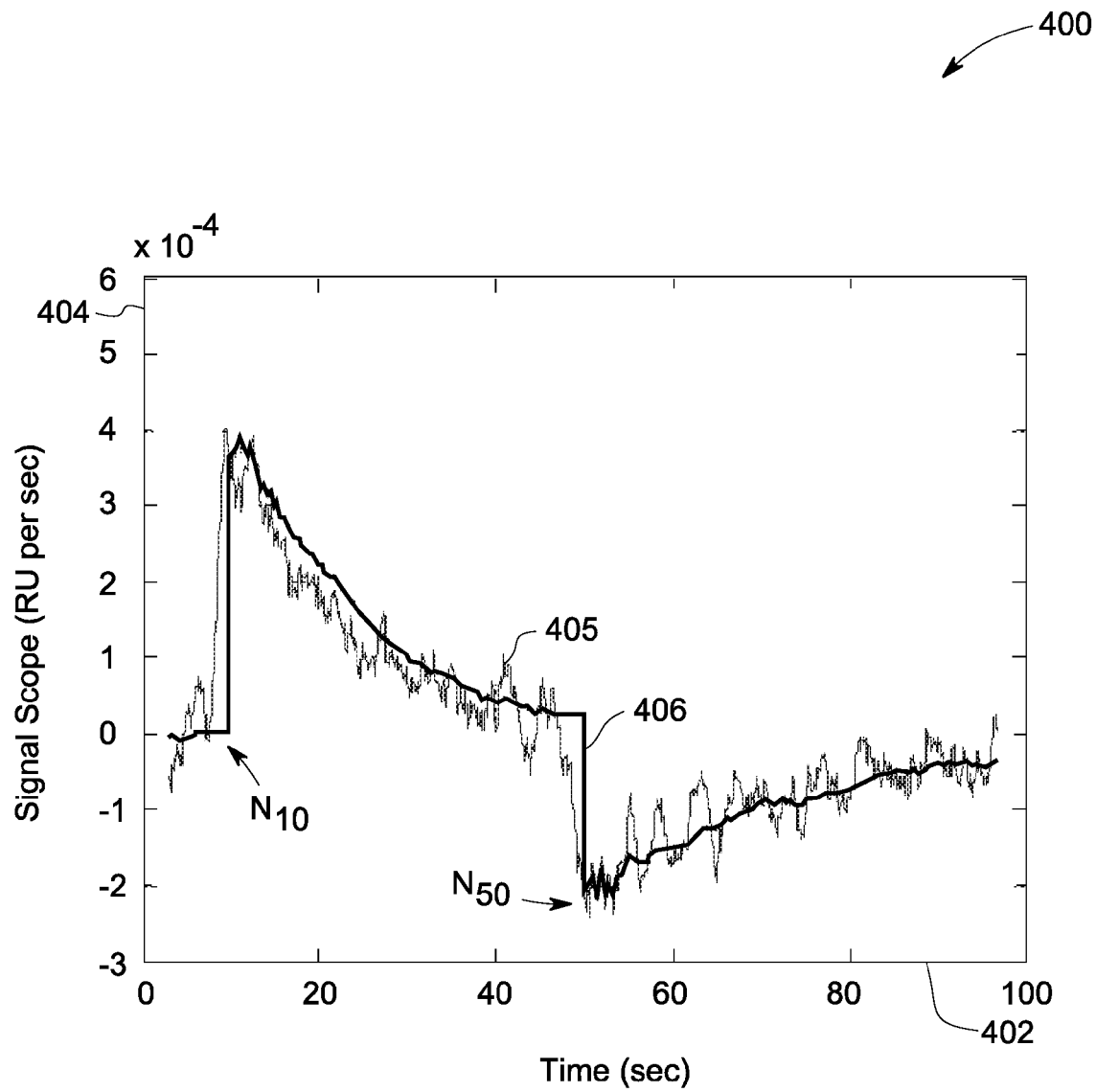
FIG. 6 is a graphical illustration of signal slope estimates by a short-window estimator and a Kalman estimator associated with said example in accordance with an embodiment of the present invention.

FIG. 6 is a graphical illustration 400 of signal slope estimates for the linear filtering method by employing an optimal combination of a Short-window estimator and a Kalman estimator. The X-axis 402 represents time in seconds. The Y-axis 404 represents signal slope in RU per second. The signal slopes represented by the Short window estimator and Kalman estimator are 405 and 406 respectively. As shown, the short-window estimate is much noisier than the Kalman estimate, but responds quickly to the abrupt change in signal slope at the event times $N_{10}$ and $N_{50}$ (also illustrated in FIG. 5). On the other hand, the Kalman filter has a smoother estimate, but is sluggish to abrupt changes. At the event times $N_{10}$ and $N_{50}$, the Kalman estimate is reset to the short-window estimate, so that the abrupt change in signal slope can be captured. Thus, by using event timing information, the Kalman estimator is reset to the result of the short-window estimator, thus re-starting the filter, at the onset of injection events. This results in an accurate estimate of signal slope that also responds quickly to abrupt changes in the signal around event times. The magnitude of the Kalman estimate is inversely mapped to the filter length. The filter length generated by a slope-based filter length generator decreases abruptly when signal slope increases abruptly after an injection event, then returns to the maximum length as signal slope decreases towards steady state.

Figure 7:
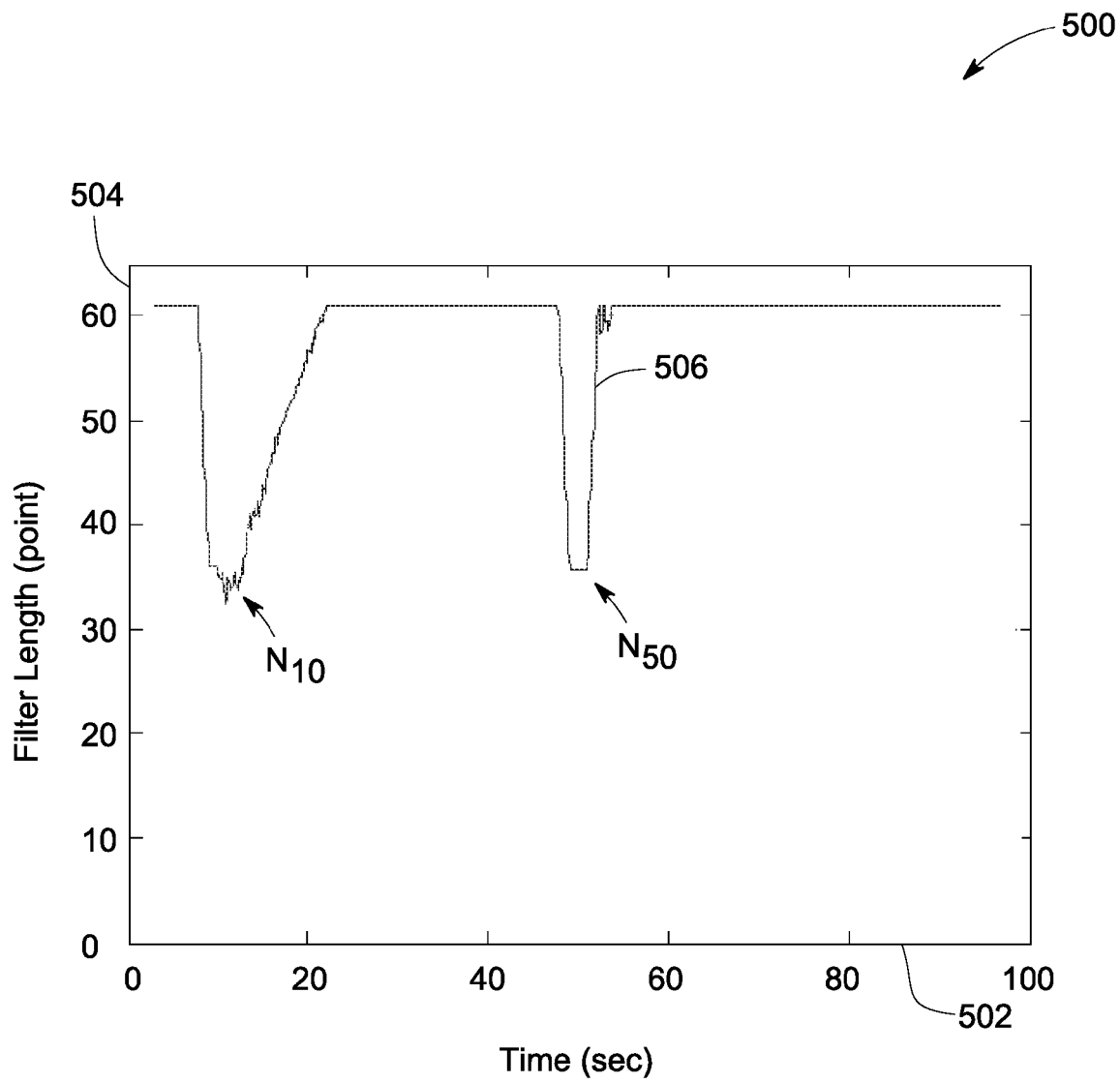
FIG. 7 is a graphical illustration of a plot of filter length and time for said example in accordance with an embodiment of the present invention.

FIG. 7 illustrates a plot 500 of filter length versus time for the above-mentioned example in accordance with an exemplary embodiment of the present invention. The X-axis 502 represents time in seconds. The Y-axis 504 shows filter length represented in point units. The adaptive feature of the linear filtering algorithm causes the filter length represented by 506 to be around 35 points around the event times ($N_{10}$ and $N_{50}$) at 10 seconds (after the start of association) and 50 seconds (after the start of dissociation). At event times $N_{10}$ and $N_{50}$, the algorithm reduces the filter length to limit the distortion in the SPR signal and preserve the abrupt signal changes around the events. It is to be noted that the filter length used by the linear filtering method is the lesser of the output of a slope-based filter length generator and an event-based filter length generator. The event-based filter length generator, before and after an interval about each event, varies filter length linearly from the maximum to the minimum and then back to the maximum.

Advantageously, the various embodiments of the invention provide noise reduction in SPR sensorgrams. Thus, the linear filtering method employs a dynamic filtering scheme that not only reduces or eliminates noises but also preserves the SPR signals in the sensorgrams so that the SPR sensorgram is substantially capable of highlighting features, which are indicative of critical biochemical process or event such as the onset of a binding event between analytes and ligands within a sample. Furthermore, the use of a symmetric FIR filter eliminates the possibility of phase distortion that other linear or nonlinear filters may introduce.

Furthermore, the skilled artisan will recognize the interchangeability of various features from different embodiments. For example, the adaptive filter of a linear filtering method can be generated in real-time and based either only on event timings or slopes exclusively. Similarly, the various method steps and features described, as well as other known equivalents for each such methods and feature, can be mixed and matched by one of ordinary skill in this art to construct additional systems and techniques in accordance with principles of this disclosure.

Of course, it is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for linear filtering of noise in a sensorgram generated from a surface plasmon resonance apparatus, the method comprising:
providing a linear filter of variable length to filter an output signal in the sensorgram; and
determining an optimal length of the linear filter based on a slope of the signal in the sensorgram and a plurality of timing of occurrences of events during measurement of refractive index in the apparatus to reduce noise in the sensorgram.

2. The method of claim 1, wherein the linear filter provided comprises a symmetric finite impulse response filter.

3. The method of claim 1, wherein the linear filter provided comprises a variable-length symmetric moving average filter.

4. The method of claim 1, wherein the filter length varies dynamically for ensuring the signal in the sensorgram to preserve characteristics indicative of a critical biochemical process.

5. The method of claim 1, further determining a longer filter length when variations in the signal decreases.

6. The method of claim 1, further determining a shorter filter length when variations in the signal increases.

7. The method of claim 1, wherein the events are an indicative of a start of association and dissociation of reactants in a biochemical process.

8. The method of claim 7, wherein the events comprise opening and closing of a plurality of valves in the surface plasmon resonance apparatus.

9. The method of claim 8, wherein the events comprise a plurality of distances between the valves in the apparatus.

10. The method of claim 1, wherein the events comprise a plurality of distances between a plurality of transducers in the apparatus.

11. The method of claim 1, wherein the events comprise flow rates in the apparatus.

12. A method for linear filtering of noise in a sensorgram generated from a surface plasmon resonance apparatus, the method comprising:
providing a linear filter of variable length to filter an output signal in the sensorgram;
determining a first filter length based on a plurality of timings of occurrences of events during measurement of surface plasmon resonance in the apparatus;
determining a second filter length based on a slope of the signal between the plurality of events;
comparing the first filter length and the second filter length; and
selecting a shorter length between the first filter length and the second filter length.

13. The method of claim 12, further providing the first filter length based on determining a plurality of event times and estimating significance of the events.

14. The method of claim 12, further providing the second filter length based on an instantaneous slope of the signal.

15. The method of claim 12, further providing a filtering algorithm based on real-time characteristics wherein an output is delayed by a specified amount.

16. A linear filtering system for filtering noise in a surface plasmon resonance sensorgram, the system comprising:
a SPR measurement apparatus for generating a sensorgram;
a processor for receiving the sensorgram, which processor is configured to:
provide a linear filter of variable length to filter an output signal in the sensorgram;
determine a first filter length based on a plurality of timings of occurrences of events during measurement of refractive index in the apparatus;
determine a second filter length based on a slope of a signal between the plurality of events;
compare the first filter length and the second filter length; and
select a shorter length between the first filter length and the second filter length.

17. The system of claim 16, wherein the SPR measurement apparatus comprises an optical source, an optical detection unit, a SPR transducer, an output device, a metal film and a flow channel system.

18. The system of claim 16, wherein the optical source generates a light beam.

19. The system of claim 16, wherein the SPR transducer further comprising a prism, a glass slide with a thin optically reflective backing, and a binding layer.

20. The system of claim 16, wherein the optical detection unit intercepts optical signals reflected from the SPR transducer and provides the surface plasmon resonance sensorgram.

* * * * *